United States Patent [19]

Retzinger et al.

[11] Patent Number: 5,658,588
[45] Date of Patent: Aug. 19, 1997

[54] FIBRINOGEN-COATED LIPOSOMES

[75] Inventors: Gregory Scott Retzinger; Ashley P. Deanglis, both of Cincinnati, Ohio

[73] Assignee: University of Cincinnati, Cincinnati, Ohio

[21] Appl. No.: 414,368

[22] Filed: Mar. 31, 1995

[51] Int. Cl.$^6$ ................................................. A61K 9/127
[52] U.S. Cl. ............................ 424/450; 514/2; 514/21
[58] Field of Search ...................... 424/450; 436/829; 264/4.1, 4.3; 514/2, 21

[56] References Cited

U.S. PATENT DOCUMENTS

| | | | |
|---|---|---|---|
| 4,377,567 | 3/1983 | Geho | 424/1 |
| 4,394,448 | 7/1983 | Szoka, Jr. et al. | 435/172 |
| 4,647,536 | 3/1987 | Mosbach et al. | 435/177 |
| 4,913,902 | 4/1990 | Kilpatrick | 424/85.8 |
| 5,013,556 | 5/1991 | Woodle et al. | 424/450 |
| 5,206,023 | 4/1993 | Hunziker | 424/423 |
| 5,264,221 | 11/1993 | Tagawa et al. | 424/450 |
| 5,283,122 | 2/1994 | Huang et al. | 428/402.2 |
| 5,283,185 | 2/1994 | Epand et al. | 435/172.3 |

FOREIGN PATENT DOCUMENTS

| | | |
|---|---|---|
| 0485210 | 5/1992 | European Pat. Off. . |
| 9214447 | 9/1992 | WIPO . |
| 9214445 | 9/1992 | WIPO . |
| 9305067 | 3/1993 | WIPO . |

OTHER PUBLICATIONS

Gibble and Ness, Transfusion 30 (1990): 741–747.
Kram, et al., Am. Surg. 57 (1991): 381–384.
Redl, et al., Thorac. Cardiovasc. Surgeon 30 (1982): 223–227.
Baldassare, et al, J. Clin. Invest. 75 (1985): 35–39.
Rybak, et al., Biomet., Art. Cells & Immob. Biotech. 21(2): 101–118 (1993).
Alving, J. Immun. Methods 140 (1991): 1–13.

*Primary Examiner*—Gollamudi S. Kishore
*Attorney, Agent, or Firm*—Frost & Jocobs

[57] ABSTRACT

A method for preparing fibrinogen-coated liposomes is disclosed. In this process, fibrinogen and an acylating agent are reacted in the presence of a dispersion of liposomes under specifically defined reaction conditions. The liposomes formed using this process, pharmaceutical compositions containing those liposomes, and the methods of clotting blood and delivering pharmaceutically-active agents and/or other chemicals utilizing those pharmaceutical compositions are also disclosed.

36 Claims, No Drawings

FIBRINOGEN-COATED LIPOSOMES

The present invention relates to the placement of fibrinogen onto surfaces for the purpose of rendering that surface physiologically adhesive and, in particular, to the placement of fibrinogen onto liposome structures which are used to enhance blood clotting at wound sites and to deliver pharmaceutical agents and/or other chemicals to specific sites in vivo or in vitro.

BACKGROUND OF THE INVENTION

Hemorrhage is a major cause of the morbidity and mortality associated with traumatic cardiovascular injury, whether this injury is sustained on the battlefield, during a vehicular collision, or in the operating room. Rapid control of hemorrhage, especially in a chaotic setting, would undoubtedly reduce this morbidity and mortality. One very promising method for such control involves mimicry of the body's own hemostatic system: a concentrated solution of fibrinogen (the precursor of the protein matrix of blood clots) and thrombin (the mammalian enzyme that catalyzes fibrin formation) is applied topically to a bleeding wound. The separate but simultaneous application of substrate (i.e., fibrinogen) and catalyst (i.e., thrombin) results in the rapid formation of a fibrin clot at the site of application. The fibrin thus formed promotes not only local hemostasis but also wound healing. While this approach has been used with some success, it does not effectively control bleeding from larger wounds. In the body's natural clotting system, platelets work synergistically with fibrin to control hemorrhage. The physical size of the platelets helps plug the wound opening. The use of fibrin without platelet bodies is not nearly as effective in controlling bleeding as are the two together, particularly from larger wound sites.

The use of platelets to control bleeding, however, presents some very practical problems. For example, platelets have a very short shelf life and require rigorous storage temperature and mixing conditions to maintain their efficacy in vivo. This makes platelets impractical for use in large scale emergency trauma situations, particularly in non-hospital settings. Therefore, it would be very useful to develop a composition which mimics the blood clotting efficacy of platelets, but which does not have the same storage problems which they typically present.

When used together with thrombin as catalyst, fibrinogen effectively limits bleeding from smaller wounds. See, for example, Gibble and Ness, Transfusion 30 (1990) 741–747; Kram, Shoemaker, Clark, Macabee and Yamaguchi, Am. Surg. 57 (1991) 381–384; and Redl, Schlag and Dinges, Thorac. Cardiovasc. Surgeon 30 (1982) 223–227. See also, U.S. Pat. No. 4,647,536, Mosbach, et al, issued Mar. 3, 1987, which describes the encapsulation of viable animal or plant cells in polymer beads made from agar, agarose or fibrinogen; and European Patent Application 0 485 210, published May 13, 1992, which describes fibrous protein membranes, at least a portion of which is formed from fibrin, used to dress wounds, inhibit bleeding and deliver drugs to the wound site.

In addition, liposomes are very well known for the delivery of pharmaceutical actives to various sites in the human body. For example, U.S. Pat. No. 4,394,448, Szoka, Jr., et al, issued Jul. 19, 1983, describes lipid vesicles which encapsulate DNA or DNA fragments and are used to insert those DNA materials into living cells.

U.S. Pat. No. 5,264,221, Tagawa, et al, issued Nov. 23, 1993, describes drug-containing liposomes which have specifically defined targeting agents on their surface. These targeting agents are thiol-containing proteins and residues of thiol-containing compounds which include a polyalkylene glycol moiety bound to a maleimide residue on the surface of the liposome.

U.S. Pat. No. 5,283,122, Huang, et al, issued Feb. 1, 1994, describes fused liposomes and their use as delivery vehicles for pharmaceutical agents. An acid-induced liposome fusion procedure is disclosed.

PCT Patent Application WO 92/1447, Baxter International, published Sep. 3, 1992, describes liposomes used for drug delivery. The surface of those liposomes contains specific residues (i.e., glutaraldehyde and water-soluble carbodiimide) which are crosslinked to targeting agents such as gelatin, collagen, and hyaluronic acid. See also, PCT Patent Application WO 92/14445, Baxter International, published Sep. 3, 1992.

The use of platelet-derived proteins in liposomes has also been disclosed. Baldassare, et al, J. Clin. Invest. 75 (1985), 35–39, describes the incorporation of platelet glycoproteins IIb and IIIa into phospholipid vesicles. It was found that those proteins in the vesicles have similar physiological properties as they do in platelets. Rybak, et al, Biomat., Art. Cells & Immob. Biotech., 21(2), 101–118 (1993), describes the incorporation of an undefined mixture of platelet proteins into liposomes. This product was shown to have an effect in stopping wound bleeding. Neither of these papers discuss the incorporation of fibrinogen into any liposome structures.

Although not previously suggested by the art, the incorporation of fibrinogen into a liposome structure could provide many advantages. For example, assuming the liposomes could be coated with functional fibrinogen, they could provide rapid, biomimetic control of wound hemorrhage even in the chaotic setting of a trauma scene. These liposomes could not only provide hemostatic, but also wound healing, benefits. Large quantities of the liposomes could be produced at low cost and on demand. They could be more effective at facilitating hemostasis than the fibrin glues described in the art, without having the storage stability and logistical problems inherent in the use of platelets as a hemostatic agent. They could be stored indefinitely at room temperature in a lyophilized state. Once reconstituted in aqueous phase, their shelf life could be made indefinite by addition of antibiotics to the storage medium. In addition, use of such liposomes could be virtually without risk of blood-borne infection to the recipient.

Unfortunately, conventional approaches for binding proteins to liposomes do not work effectively with fibrinogen to provide a final product which has adhesive properties. Most of these approaches involve the use of a bifunctional reagent that cross-links a reactive group contributed by a liposomal component to a reactive group contributed by the protein. In the case of fibrinogen, such approaches do not yield liposomes coated densely with demonstrably functional protein. Acylation of the fibrinogen prior to incorporating it into liposomes is also problematic. In the absence of liposomes or other amphiphilic/hydrophobic surfaces, the acylation of fibrinogen yields an insoluble, amorphous material unsuitable for coating liposomes.

The present invention relates to a method for effectively incorporating fibrinogen onto the surface of liposome-like (e.g., cell membrane) structures or any amphiphilic or hydrophobic surface. It further encompasses the fibrinogen-coated liposome structures, themselves, and pharmaceutical compositions containing those structures. Those compositions can be used as platelet-like biochemical hemostats, drug delivery systems which target sites of inflammation and/or clotting, reagents for the imaging of clot-containing lesions, reagents for clinical, clot-based coagulation assays, a bioadhesive reagent to introduce molecules into cells or facilitate adhesion between chemical reactants, an adhesive reagent for facilitating chemical reactions between environmentally-incompatible reactants, a vaccine component or an adjuvant for vaccines, a reagent for modifying the lipid composition of biological membranes, and a reagent for transfection of genes into target cells.

SUMMARY OF THE INVENTION

The present invention relates to a method for preparing fibrinogen-coated liposomes comprising reacting fibrinogen and an acylating agent in the presence of a dispersion of liposomes at a buffered pH of from about 6.5 to about 8.5, and a temperature of from about 0° C. to about 50° C., wherein the molar ratio of said acylating agent to said fibrinogen is from about 1:1 to about 5,000:1, and there is sufficient fibrinogen present to form a film on the surface of said liposomes.

The present invention also relates to liposomes made by this process wherein a hemostatically/adhesively effective mount of a hydrophobic fibrinogen material is covalently incorporated into the lipid bilayer of said liposome. These liposomes may have pharmaceutically-active agents, such as anti-inflammatory agents and clot dissolving agents, dyes, nucleic acids or other chemicals, incorporated within them. Pharmaceutical compositions, both for topical and parenteral administration, incorporating said liposomes and a pharmaceutically-acceptable compatible carrier, are also disclosed. Also described are methods for using the liposomes of the present invention to clot blood at a wound site, and to deliver pharmaceutically-active agents or chemicals to any fibrin- or fibrinogen-rich focus in vivo or in vitro.

DETAILED DESCRIPTION OF THE INVENTION

As used herein, all percentages and ratios are "by weight" unless otherwise specified.

The phrase "safe and effective amount", as used herein, means sufficient amount of the component being defined (i.e., the liposomes or the pharmaceutical active within the liposomes) to provide the desired pharmaceutical benefit, at a reasonable benefit/risk ratio attendant with any medical treatment. Within the scope of sound medical judgment, the required dose of liposome or pharmaceutical component contained within the liposome will vary with the nature and severity of the condition being treated, the duration of the treatment, the nature of adjunct treatment, the age and physical condition of the patient, the specific pharmaceutical actives being employed, and like considerations more fully discussed hereinafter.

"Pharmaceutically acceptable", as used herein, means that the ingredients used in the present invention are suitable for use in contact with the tissues of humans and lower animals without undue toxicity, irritation, allergic response, and the like, commensurate with a reasonable benefit/risk ratio.

By "compatible" herein is meant that the components of the present invention are capable of being commingled without interacting in a manner which would substantially decrease their efficacy under ordinary use conditions.

Fibrinogen-coated liposomes of the present invention are produced by reacting fibrinogen and an acylating agent in the presence of a dispersion of liposomes under specific reaction conditions. The various procedures, conditions and components used in this reaction, as well as the fibrinogen-coated liposomes formed by this reaction, will now be described in detail.

The fibrinogen coating described in this application can be placed on any material that has an accessible hydrophobic/amphiphilic phase. For example, an oil and water emulsion (such as an emulsion of olive oil in water) could be used, the fibrinogen coating being placed on the oil droplets in that emulsion. In another embodiment, a cell such as a tumor cell could be used. However, it is preferred that liposomes and, particularly, phospholipid liposomes be used in the present invention since they best mimic the characteristics of cell membranes. The term "liposome" as used herein means man-made lipid vesicles, created in the laboratory and characterized in part by multiple or single bimolecular lipid layers forming the vesicle walls.

For the preparation of the liposomes, any method can be used. For example, a lipid mixture having a solvent removed, is hydrated and emulsified by a homogenizer, followed by freeze-thawing to obtain multilamellar liposomes. Membrane extrusion procedures can also be used to form the liposomes used herein. To further adjust the particle size, the liposomes may be subjected to ultrasonic treatment, high speed homogenizing, or press-filtration through a membrane having uniform pores. Preparation of liposomes is described in Hope, M. J., et al, Biochimica et Biophysica Acta 812, 55 (1985); U.S. Pat. No. 5,264,211, Tagawa, et al, issued Nov. 23, 1993; U.S. Pat. No. 5,283,122, Huang, et al, issued Feb. 1, 1994; and U.S. Pat. No. 4,394,448, Szoka, Jr., et al, issued Jul. 19, 1983, all of which are incorporated herein by reference.

Materials which can be used for forming liposomes are generally well known, as are the methods for their preparation. For example, any number of phospholipid or surfactant compounds may be used to form the liposomes. Representative of such compounds are phosphatidylcholine, both naturally occurring and synthetically prepared, phosphatidic acid, lysophosphatidylcholine, phosphatidylserine, phosphatidylethanolamine, sphingolipids, phosphatidylglycerol, sphingomyelin, cardiolipin, glycolipids, gangliosides, cerebrosides, and the like, used either singly or intermixed such as in soybean phospholipids. In addition, other lipids, such as steroids, cholesterol, aliphatic amines, such as long chain aliphatic amines and carboxylic acids, long chain sulfates and phosphates, dicetyl phosphate, butylated hydroxy-toluene, tocopherol, retinol, and isoprenoid compounds may be intermixed with the phospholipid components to confer certain desired and known properties on the formed liposomes. Preferred liposome forming compounds used in the present invention include lecithin, cholesterol, and mixtures thereof.

Following dissolution of the phospholipid or lipid in an inert organic solvent (e.g., diethyl ether or THF) to form the organic phase, an aqueous phase is added to obtain a heterogeneous two-phase mixture. The aqueous phase contains in dissolution/suspension any pharmaceutical materials which are to be encapsulated in the liposomes. The pH and ionic strength of the aqueous phase should be controlled as appropriate to maximize stability and encapsulation efficiency. The heterogeneous two-phase mixture is then emulsified to obtain an emulsion of the character produced by ultrasonic radiation. Preferably, this is accomplished by using a bath-type sonicator or, for large volume preparations, an industrial size emulsifier. The optimum conditions under which emulsification is carried out depends upon the solvent, lipid, and volume of aqueous phase used in the preparation. Trial and error techniques may be used to determine the optimum conditions for emulsification. The emulsion mixture is then treated to remove a substantial portion of the inert organic solvent. This may be carried out conveniently by use of a rotary evaporator, preferably at a temperature of from about 20° C. to about 60° C. under reduced pressure. The precise conditions to be used will depend upon the identity of the organic solvent, as well as any pharmaceutical agent encapsulated in the liposomes. During evaporation, the emulsion becomes a viscous dispersion. The dispersion may be converted by agitation, by extrusion through a microporous membrane, or by further emulsification in an aqueous medium, such as a buffered solution, to form a homogeneous suspension of liposomes. Non-incorporated material may be removed by known techniques, such as centrifugation, chromatography or dialysis. The liposomes can be suspended in any isotonic buffer for use. If desired, the liposomes may be sterilized by passage through a micropore filter.

For use in the present invention, it is preferred that the liposomes have an average particle size of from about 0.05 to about 20 microns to most effectively mimic the character of platelets. Preferred liposomes have a particle size (i.e., average diameter) of from about 0.1 to about 4 microns, more preferably from about 0.2 to about 1 micron, most preferably about 0.4 micron.

Fibrinogen is a well known, naturally occurring material. It is described in Hantgan, et al, Fibrinogen Structure and Physiology, in *Hemostasis and Thrombosis: Basic Principles and Clinical Practice*, 3rd Edition, edited by Robert W. Colman, et al, J. B. Lippincott Company, Philadelphia, 1994, incorporated herein by reference. The fibrinogen molecule is a dimeric molecule consisting of three pairs of disulfide-bonded polypeptide chains, designated $A\alpha$, $B\beta$ and $\gamma$. The nomenclature of the chains derives from the fact that relatively small polypeptides, called fibrinopeptides A and B, which constitute about 2% of the total protein content, are released from $A\alpha$ and $B\beta$ chains when thrombin acts on fibrinogen. Molecules devoid of fibrinopeptides A and/or B are referred to as fibrin monomers.

The entire amino acid sequence of human fibrinogen, a total of 1,482 residues in each set of three polypeptide chains, has been determined by classic protein chemistry techniques. There are 610, 461, and 411 amino acid residues in the common forms of the $A\alpha$, $B\beta$, and $\gamma$ chains, respectively. The computed respective molecular weights of these chains are 66,500, 52,000, and 46,500, for a total molecular weight of approximately 330,000 for two copies of each chain. Less common structural variants exist, with the most frequent one (less than 10%) being a variant of the $\gamma$ chain in which residues 408–411 have been replaced with a 20-residue sequence ending in leucine at position 427. In addition to their amino acid content, the $B\beta$ and $\gamma$ chains contain carbohydrate, each of molecular weight 2,500, attached covalently at residues 364 and 52, respectively. Thus, the computed molecular weight of fibrinogen is approximately 340,000.

The overall length of fibrinogen is 475 Angstroms (Å), and the molecule is composed of two roughly spherical nodules 65 Å in diameter connected by thin threads which are 8 Å to 15 Å in diameter to a central nodule about 50 Å in diameter.

The conversion of soluble fibrinogen into an insoluble polymer to form a blood clot at a wound site takes place in essentially three steps: (1) cleavage of fibrinopepides by thrombin resulting in the formation of fibrin monomer; (2) a three step non-covalent assembly process wherein the fibrin fragments are oriented in a specific manner; and (3) covalent stabilization of fibrin by Factor XIIIa-catalyzed crosslinking.

In order to incorporate fibrinogen into the liposomes, the protein must be treated so as to make it hydrophobic. Although any treatment which would provide fibrinogen with a hydrophobic character (e.g., acylation, alkylation or phenylation) can be used, it is preferred that this be done using a conventional acylation reaction. Acylating agents are well known and may include, for example, acid chlorides or acid anhydrides, although any conventional acylating agent may be used herein. It is preferred that the alkyl acid chain in the acylating agent contain at least 2 carbons and preferably contain from about 8 to about 20 carbons, more preferably from about 12 to about 18 carbons. The most preferred acylating agent contains about 16 carbons (palmitoyl), and is preferably palmitoyl chloride. If acylating agents having a chain length considerably greater than about 20 carbon atoms are used, the solubility of the product formed tends to decrease significantly with the resulting compound having properties less like fibrinogen than is optimum.

In performing the acylation reaction, the fatty acid group is bound to the $\epsilon$-amino functions of the lysines of the fibrinogen in such an amount that the resulting compound will associate with the liposomes but will not change the physiological character of the fibrinogen molecule itself. If shorter chain acylating agents are used, a significantly higher level of them may need to be incorporated into the fibrinogen molecule in order to get the desired result. If longer chain acylating agents are used, fewer of them may need to be incorporated into the fibrinogen molecule. In general, the resulting fibrinogen molecules contain acyl groups at from about 1% to about 95%, preferably from about 5% to about 50%, more preferably from about 20% to about 25%, of their $\epsilon$-amino functional sites. Although the precise amount of acylating agent utilized will depend upon such things as the identity of the acylating agent, the chain length of the acylating agent, and the desired properties of the resulting fibrinogen molecule, it is preferred that the molar ratio of acylating agent (e.g., palmitoyl chloride) to fibrinogen be from about 1:1 to about 5,000:1, preferably from about 500:1 to about 5,000:1, more preferably from about 2,000:1 to about 5,000:1, still more preferably from about 2,500:1 to about 5,000:1. It is most preferred that the reaction be carried out using palmitoyl chloride as the acylating agent at an acylating agent:fibrinogen molar ratio of about 2,500:1.

The acylation reaction of the fibrinogen must be carried out in the presence of the liposomes. This is usually done in a dispersion in an aqueous buffered medium (e.g., phosphate-buffered saline), although other compatible non-aqueous solvents may be used as long as the materials are well dispersed within it. As the acylation reaction takes place, the acylated fibrinogen immediately associates with the liposomes yielding the products of the present invention. If the acylation is not carried out in the presence of the liposomes, the acylated fibrinogen associates with itself, forming an insoluble mass which cannot effectively be incorporated into the liposomes.

The reaction to form the liposomes of the present invention should be carried out a temperature of from about 0° C. to about 50° C., most preferably at about room temperature. If the temperature gets too high, the fibrinogen denatures and loses its blood clotting properties. In addition, the solution in which the reaction is carried out should be buffered in order to control the pH during the acylation reaction in the range of from about 6.5 to about 8.5, preferably about 7.4. A 0.1M phosphate buffer is preferred. It is also preferred that the reaction be carried out with high energy mixing during the reaction in order to make sure that the liposomes and the fibrinogen remain well dispersed throughout the system during the reaction, allowing them to interact most efficiently. In this regard, it is preferred that the reaction be carried out in a water bath sonicator. It is also preferred that the acylating agent be added to the system containing the fibrinogen and the liposomes as a solution (e.g., in acetone, ethanol or diethyl ether) at a low and steady rate of addition (e.g., from about 0.1 to about 20.0 millimoles/liter/minute of acylating agent).

The precise amount of fibrinogen incorporated into the liposomes is difficult to define in absolute terms since it will depend upon the size of the liposomes utilized and the particular characteristics which the finished liposomes are desired to have. However, the amount to be used in a given situation may be determined by one skilled in the art based on the information provided herein. The amount of acylated fibrinogen which is incorporated into the liposomes is a hemostatically/adhesively-effective amount (i.e., that amount which will be sufficient to direct that liposome to the wound site (i.e., site of fibrin(ogen) concentration) and provide hemostatic or adhesive properties). When calculating the amount of fibrinogen to be added to the reaction, that amount should be sufficient such that the liposomes formed contain either a saturated or subsaturated film (preferably a saturated monolayer coating) of acylated fibrinogen on their surface. The precise amount this translates into depends upon the size and surface area of the liposomes utilized. However, utilizing liposomes of the size defined herein, it is preferred that from about 0.1 to about 1.0 milligram of fibrinogen, preferably from about 0.5 to about 0.8 milligram of fibrinogen, more preferably from about 0.6 to about 0.7 milligram of fibrinogen, and most preferably about 0.66 milligram of fibrinogen, per milligram of liposome be incorporated. It is generally preferred that the acylated fibrinogen molecules be packed "end on" at the liposome surface (i.e., with respect to its long axis, each fibrinogen molecule is approximately perpendicular to the plane of the liposome surface). This will allow for the formation of a monolayer containing the greatest concentration of fibrinogen. The minimum surface area that the fibrinogen can take up at the liposome surface in this case is about 10,000 $Å^2$.

The fibrinogen-coated liposomes of the present invention may be effectively utilized as excellent hemostatic agents, without containing any encapsulated pharmaceutical compounds. However, the liposomes of the present invention may also contain pharmaceutically-active agents within them. In this configuration, the liposomes may be used to target those specific pharmaceutically-active agents to, for example, a site of intimation or blood clots (i.e., any site at which fibrin would be present). Examples of pharmaceutical agents which may be encapsulated within the liposomes of the present invention include anti-inflammatory agents (e.g., aspirin, ibuprofen, indocin, prostacyclin, a phospholipase $A_2$ inhibitor, interleukin or lymphokine), clot dissolving agents (e.g., plasmin, plasminogen, tissue plasminogen activator, urokinase, streptokinase or atroxin), and mixtures thereof. Radiopaque materials may also be encapsulated within the liposomes in order to provide reagents for imaging fibrin (ogen) containing lesions. The presence of such agents allows the physician to monitor the progression of wound healing occurring internally, such as at the liver, gall bladder, heart, lungs, brain, bone, gastrointestinal tract, or blood vessels. Such agents include barium sulfate, as well as various organic compounds containing iodine. Examples of such compounds include iocetamic acid, iodipamide, iodoxamate meglumine, iopanoic acid, as well as diatrizoate derivatives such as diatrizoate sodium. Various reagents (such as dye, clotting factors, heparin or chromogenic polypeptide substrates) can also be incorporated within the liposomes in order to carry out clinical, clot-based coagulation assays. Finally, nucleic acids and/or their analogues, such as those described in U.S. Pat. No. 4,394,448, Szoka, Jr., et al, issued Jul. 19, 1983, may be incorporated into the liposomes as a means for inserting that material into cells, for example, in gene therapy.

The pharmaceutical compositions of the present invention may be formulated for a variety of uses, such as control of clotting at wound sites, the targeted delivery of pharmaceutical agents to sites where fibrin is present, use as an imaging agent at fibrin(ogen)-containing lesion sites, and the insertion of nucleic acids and/or their analogues into specific cell sites. Specific components included in the pharmaceutical compositions will vary depending on the use envisioned for those compositions. Where control of clotting or drug delivery is to be desired, the composition may be formulated either for topical or parenteral use. The pharmaceutically-acceptable carriers utilized in the present invention are those conventionally known and used. Any pharmaceutically-acceptable carrier which is compatible with the liposomes of the present invention and with the blood may be used in formulating the compositions of the present invention. For example, suitable carriers are aqueous solutions including electrolyte solutions, sugar solutions, or saline solutions. The aqueous component of these solutions should be pyrogen-free water, buffered as appropriate. Such solutions can be used whether administered topically or parentally.

In such compositions, a safe and effective amount of the liposome component is utilized in order to achieve the desired pharmaceutical result. Preferably, the compositions contain from about 0.001% to about 98%, more preferably from about 25% to about 90% of the liposomes. The balance of the compositions is the pharmaceutically acceptable carrier.

When used for the control of clotting, the pharmaceutical compositions of the present invention may additionally contain a component which covalently crosslinks fibrin to fibrin in order to assist in forming the blood clot. Useful materials are selected from the class of transglutaminases, such as F XIII, which is converted to F XIIIa by thrombin at the wound site. This material covalently stabilizes the hemostatic liposomes at the wound site. It is included in the compositions of the present invention in an amount of from about 0.0001% to about 5%. Another component which may be usefully included in such compositions is a vasoconstrictor which, by promoting local vasoconstriction, decreases blood flow from incised vessels at the wound site. An example of such a material is angiotensin II, which would be utilized in the compositions of the present invention in an amount of from about $1 \times 10^{-8}$% to about 1%. Finally, the pharmaceutical compositions of the present invention may include a component which inhibits fibrinolysis, i.e., premature lysis of the hemostatic seal. An example of such a material is EACA (ε-Amino caproic acid) which is usefully incorporated in the compositions of the present invention in an amount of from about 0.0001% to about 5%. In addition to being formulated and applied as an aqueous dispersion, the blood clotting compositions of the present invention may also be formulated as spray or aerosol compositions which are sprayed onto the wound site, or incorporated into dressing material, i.e., fabric, which is applied to a wound site.

Topical treatment regimens of the present invention comprise applying the compositions herein directly to the skin at the site of the wound to be treated. The rate of application and duration of treatment will depend upon the severity of the condition, the response of the particular patient, and related factors within the sound medical judgement of the attending physician or patient. In general, from about 0.1 to about 50.0 milligrams of liposomes per square centimeter of afflicted situs are used. An effective amount of thrombin (i.e., from about 0.01 NIH unit to about 5.0 NIH units per square centimeter of skin) should also be added to the wound site to catalyze the blood clot formation. Application can be made once or several times to control the bleeding from a wound or may be made over the course of a more extended period of time where drug delivery to the situs or promotion of wound healing is desired.

Where the pharmaceutical compositions of the present invention are to be administered parenterally, a safe and effective amount of the composition (preferably from about 0.5 to about 50 ml/minute) is given to the patient either subcutaneously, intramuscularly or intravenously.

The following non-limiting examples illustrate the present invention, but are not intended to be limiting thereof.

EXAMPLE 1

Chemicals and Reagents—Human fibrinogen, grade L, from Kabi AB (Stockholm, Sweden) is desalted using gel permeation chromatography and then equilibrated in phosphate buffer containing 0.10M $Na_2HPO_4$ and $NaH_2PO_4$, pH 7.40, and 0.145M NaCl (PBS). This fibrinogen is stored at $-20°$ C. until use. The fibrinogen concentration of the solutions is determined using the molar absorptivity of the protein at 280 nm, $5.12 \times 10^5 M^{-1} cm^{-1}$. Before use, a frozen aliquot of fibrinogen is first thawed to room temperature and then heated to 37° C. to dissolve any residual cryoprecipitate. For some experiments, the fibrinogen is uniformly labeled using $Na^{125}I$ from Amersham (Arlington Heights, Ill.) and Iodo-Gen from Pierce (Rockford, Ill.) according to an established procedure. O-Phthaldialdehyde is from Sigma (St. Louis, Mo.). Palmitoyl chloride is from Aldrich (Milwaukee, Wis.). Egg yolk 1-α-lecithin from Avanti Polar Lipids (Birmingham, Ala.) and cholesterol from Fisher (Fair Lawn, N.J.) are dissolved in hexane:ethanol, 9:1, v/v, and stored under nitrogen at $-20°$ C. until use. 1-Palmitoyl-2-[(1-$^{14}$C]oleoyl-L-3-phosphatidylcholine ([$^{14}$C]PC) Of specific activity 1.96 $GBq \cdot mmol^{-1}$ is from Amersham. Water is deionized and distilled using an all-glass apparatus. All other chemicals are of the highest quality available commercially.

Preparation Of Fibrinogen-Coated Liposomes—The method used to prepare fibrinogen-coated liposomes involves, first, the production of liposomes and, second, the palmitoylation of fibrinogen in the presence of the preformed liposomes. Lecithin/cholesterol liposomes are prepared according to a membrane extrusion method using a commercially available apparatus (Avestin, Ottawa, Canada). Lecithin and cholesterol at a membrane-mimetic mole ratio, 7:3, are first coated onto the wall of a round bottom glass tube. The dry lipids are then dispersed in PBS using an ultrasonic water bath. Liposomes are produced by passing the lipid emulsion repeatedly through a polycarbonate membrane having pores 400 nm in diameter. The diameter of the liposomes is determined by the pore size of the membrane used during the extrusion method. Liposomes produced using this method are unilamellar. To 2.0 mL of PBS containing 40 mg of liposomes is added an equivalent volume of PBS containing 9.0 µM fibrinogen. This mixture is then dispersed at room temperature continuously for 15 minutes using an ultrasonic waterbath. At the start of this sonication, 25 µl of palmitoyl chloride dissolved in a equivalent volume of acetone is added slowly to the dispersion. Once coated with fibrinogen, the density of the liposomes increases appreciably, approaching that of fibrinogen. Consequently, the liposomes can be pelleted by centrifugation at 1500 g for 15 minutes and then washed with buffer to remove any unbound protein.

Gel Permeation Chromatography—Fibrinogen-coated liposomes are also separated from unbound fibrinogen using gel permeation chromatography. The column for this purpose is of dimensions 45.0 cm×1.6 cm. The matrix material is Sepharose CL-2B (Pharmacia, Uppsala, Sweden). The flow rate of the mobile phase, PBS, is 40.0 $mL \cdot h^{-1}$. When necessary, the elution of fibrinogen is monitored using $^{125}I$-labeled fibrinogen. Because light-scattering at lower wavelengths is problematic, the elution of liposomes and microemulsified phosphatidic acid is monitored using the "apparent" absorbance of the effluent at 500 nm.

Determination of Stoichiometries—o—Phthaldialdehyde is used according to an established technique to determine the relative percentage of amino groups of fibrinogen left unmodified by the acylation procedure. The number of palmitoylated fibrinogen molecules incorporated into a given weight of liposomes is determined using $^{125}I$-labeled fibrinogen and liposomes containing [$^{14}$C]PC. The liposomes formed using this procedure are saturated in that they contain a dense film of acylated fibrinogen on their surface in an amount of about 0.66 milligram of fibrinogen per milligram of liposome.

Animal Studies—Approximately 3.0 milligrams of these liposomes in a saline solution are applied topically along with 3 NIH units of thrombin to a 2 cm long, 2 mm deep, abdominal incisional wound of a thrombocytopenic rat (application site=about 2 $cm^2$).

Results—Bleeding is effectively stopped by the formation of a blood clot at the wound site.

EXAMPLE 2

Preparation of Fibrinogen-Coated Liposomes—The method used to prepare liposomes of the present invention is as described in Example 1 with the following changes. The PBS used during the emulsification step includes barium sulfate, 10.0 mg/ml. Using gel permeation chromatography, free barium sulfate is separated from that which has been encapsulated within the liposomes. Barium sulfate-containing liposomes are then coated with acylated fibrinogen as described in Example 1. Those fibrinogen-coated liposomes are then dispersed to a final concentration of ~10 mg/ml in PBS to form a pharmaceutical composition of the present invention.

Animal Studies—A nasogastric canula is introduced into a mouse via the mouth of the animal. The canula is inserted to the fundus of the stomach. Once in place, the rough end of the canula is used to create a 2.0 mm diameter perforation in the gastric mucosa. One ml of the pharmaceutical composition is then injected through the canula into the stomach. After removing unbound liposomes from the stomach by purging that organ using PBS, the radioopaque contrast material is visualized using traditional radiographic imaging techniques.

Results—The stomach perforation is clearly visible as a radioopaque focus in radiographic films.

EXAMPLE 3

Preparation of Fibrinogen-Coated Liposomes—The method used to prepare liposomes of the present invention is as described in Example 1 with the following changes. The PBS used during the emulsification step includes streptokinase (Kabi Vitrum), 1,000,000 units per ml. Using gel permeation chromatography, free streptokinase is separated from that which has been encapsulated within the liposomes. Streptokinase-containing liposomes are then coated with acylated $^{125}$I-fibrinogen as described in Example 1. These fibrinogen-coated liposomes are then dispersed to a final concentration of ~10 mg/ml in PBS to form a pharmaceutical composition of the present invention.

Animal Studies—Using radiographic imaging techniques and a three lumen catheter, 5.0 NIH units of human thrombin are introduced into the left anterior descending (LAD) coronary artery of a goat. Within 10 minutes, the LAD is completely occluded, and the animal suffers a severe myocardial infarction. Three ml of the pharmaceutical composition are then injected directly into the fibrin clot.

Results—Using a sonographic imaging device, it is shown that 15 minutes after having administered the liposomes, blood flow through the vessel is restored to ~50%. Additionally, at this time 60% of the administered radioactivity is located at the site of the infarction.

EXAMPLE 4

Preparation of Fibrinogen-Coated Liposomes—The method used to prepare liposomes of the present invention is as described in Example 1 with the following changes. The palmitoyl chloride is added slowly to liposomes in PBS containing fibrinogen and a nonamer of the peptide asparagine-alanine-asparagine-proline (i.e., NANP). The molar ratio of fibrinogen to nonameric NANP is 5:1. Unreacted NANP and fibrinogen are separated from the liposomes using gel permeation chromotography. The liposomes are adjusted to a final concentration of ~10 mg/ml in PBS to form a pharmaceutical composition of the present invention.

Animal Studies—One quarter milliliter of the pharmaceutical composition is injected into each of the hind footpads of 10-week-old, female, C57/BL6 mice. Two and six weeks after this injection, the titre of antibody directed against NANP is determined using an enzyme-linked immunosorbent assay.

Results—In liposome-treated animals, the titre of antibodies directed against NANP is greater than 10 times that in control animals immunized with NANP alone.

What is claimed is:

1. A liposome wherein a hemostatically effective amount of a $C_8$–$C_{20}$ acylated fibrinogen is covalently incorporated into the lipid bilayer of said liposome.

2. A liposome according to claim 1 which is formed from phospholipid materials selected from the group consisting of phosphatidylcholine, phosphatidic acid, lysophosphatidylcholine, phosphatidylserine, phosphatidylethanolamine, sphingolipids, phosphatidylglycerol, sphingomyelin, cardiolipin, glycolipids, gangliosides, cerebrosides, and mixtures thereof.

3. A liposome according to claim 2 having a size of from about 0.05 to about 20 microns.

4. A liposome according to claim 3 having a saturated or subsaturated film of acylated fibrinogen on the liposome surface.

5. A liposome according to claim 4 wherein the acylated fibrinogen is a $C_{12}$–$C_{18}$ acylated fibrinogen.

6. A liposome according to claim 5 wherein from about 1% to about 95% of the ε-amino functional sites of the lysines of the fibrinogen are acylated.

7. A liposome according to claim 6 wherein the acylated fibrinogen is a $C_{16}$ acylated fibrinogen.

8. A liposome according to claim 7 having a size of from about 0.2 to about 1 micron.

9. A liposome according to claim 8 having a size of about 0.4 micron.

10. A liposome according to claim 5 containing from about 0.1 to about 1.0 milligram of acylated fibrinogen per milligram of liposome.

11. A liposome according to claim 8 containing from about 0.6 to about 0.7 mg. of acylated fibrinogen per milligram of liposome.

12. A liposome according to claim 11 wherein from about 20% to about 25% of the ε-amino functional sites of the lysines of fibrinogen are acylated.

13. A liposome according to claim 6 which additionally comprises a safe and effective amount of a pharmaceutically-active agent incorporated within said liposome.

14. A liposome according to claim 13 wherein said pharmaceutically active agent is selected from the group consisting of anti-inflammatory agents, clot dissolving agents, radiodiagnostic agents, and mixtures thereof.

15. A liposome according to claim 6 which additionally comprises a safe and effective amount of nucleic acids incorporated within said liposome.

16. A pharmaceutical composition comprising a safe and effective amount of the liposome according to claim 6, and the balance of said composition being a pharmaceutically-acceptable compatible carrier.

17. A pharmaceutical composition according to claim 16 which comprises from about 0.001% to about 98% of said liposome.

18. A pharmaceutical composition comprising a safe and effective amount of the liposome according to claim 11, and the balance of said composition being a pharmaceutically-acceptable compatible carrier.

19. A pharmaceutical composition according to claim 18 which comprises from about 0.001% to about 98% of said liposome.

20. A pharmaceutical composition comprising a safe and effective mount of the liposome according to claim 14, and the balance being a pharmaceutically acceptable compatible carrier.

21. A pharmaceutical composition according to claim 20 which comprises from about 0.001% to about 98% of said liposome.

22. A method of preparing fibrinogen-coated liposomes comprising reacting fibrinogen and an acylating agent in the presence of a dispersion of liposomes at a buffered pH of from about 6.5 to about 8.5 and a temperature of from about 0° C. to about 50° C., wherein the molar ratio of said acylating agent to said fibrinogen is from about 1:1 to about 5,000:1, and there is sufficient fibrinogen in the reaction to form a film on the surface of said liposomes.

23. A method according to claim 22 wherein the liposomes are formed from a phospholipid material.

24. A method according to claim 23 wherein the acylating agent is selected from the group consisting of $C_8$–$C_{20}$ acid chlorides, $C_8$–$C_{20}$ acid anhydrides and mixtures thereof.

25. A method according to claim 24 wherein the acylating agent is a $C_8$–$C_{20}$ acid chloride.

26. A method according to claim 25 wherein the size of said liposomes is from about 0.05 to about 20 microns.

27. A method according to claim 26 wherein the molar ratio of acylating agent to fibrinogen is from about 2,500:1 to about 5,000:1.

28. A method according to claim 27 wherein the acylating agent is a $C_{12}$–$C_{18}$ acid chloride.

29. A method according to claim 28 wherein the liposomes have a size of from about 0.2 to about 1 micron.

30. A method according to claim 29 wherein the acylating agent is palmitoyl chloride.

31. A method according to claim 30 wherein the molar ratio of acylating agent to fibrinogen is about 2,500:1.

32. A method according to claim 31 wherein the size of the liposomes is about 0.4 microns.

33. The liposomes made according to the process of claim 22.

34. The liposomes made according to the process of claim 32.

35. A method for providing hemostasis at a wound site comprising administering a safe and effective amount of the pharmaceutical composition according to claim 17 to said wound site together with a safe and catalytically effective amount of thrombin.

36. A method for delivering a pharmaceutically active agent to the site of accumulation of fibrin or fibrinogen comprising the administration of a safe and effective mount of a pharmaceutical composition according to claim 21 to a patient in need of such treatment.

* * * * *